United States Patent
Liu et al.

(10) Patent No.: US 9,750,472 B2
(45) Date of Patent: Sep. 5, 2017

(54) SWIVEL GANTRY FOR MULTI-MODAL IMAGING SYSTEMS

(71) Applicant: KONINKLIJKE PHILIPS N.V., Eindhoven (NL)

(72) Inventors: Jinling Liu, Solon, OH (US); Dawn Barile, Highland Heights, OH (US); Steven John Plummer, Hudson, OH (US); Bruce Eliot Lutheran, Mentor, OH (US); Krassimir Todorov Krastev, Eindhoven (NL); Johannes Balthasar Maria Soetens, Esbeek (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 277 days.

(21) Appl. No.: 14/414,461

(22) PCT Filed: Jul. 1, 2013

(86) PCT No.: PCT/IB2013/055386
§ 371 (c)(1),
(2) Date: Jan. 13, 2015

(87) PCT Pub. No.: WO2014/013367
PCT Pub. Date: Jan. 23, 2014

(65) Prior Publication Data
US 2015/0164448 A1    Jun. 18, 2015

Related U.S. Application Data (60) Provisional application No. 61/672,809, filed on Jul. 18, 2012.

(51) Int. Cl.
  *A61B 5/00*    (2006.01)
  *A61B 6/00*    (2006.01)
  (Continued)

(52) U.S. Cl.
  CPC .......... *A61B 6/4417* (2013.01); *A61B 5/055* (2013.01); *A61B 6/035* (2013.01); *A61B 6/037* (2013.01);
  (Continued)

(58) Field of Classification Search
  CPC .......... A61B 6/035; A61B 6/037; A61B 5/05; A61B 6/0325; A61B 5/055; A61B 6/548; A61N 5/103; A61N 5/1037
  See application file for complete search history.

(56) References Cited

U.S. PATENT DOCUMENTS

6,661,865 B1 *  12/2003  Popilock .............. A61B 6/06
                                                  378/19
6,670,614 B1  12/2003  Plut
(Continued)

*Primary Examiner* — Joel Lamprecht (57) ABSTRACT

A multi-modal imaging system (1) includes a fixed gantry (2), and a swivel gantry (8). The fixed gantry (2) supports a first imaging modality. The swivel gantry (8) connects to the fixed gantry (2) by at least three mounting points (10) and supports a second imaging modality. Selectively the swivel gantry (8) includes a swivel frame (16) and at least three mounting points (10) for mounting the fixed and swivel gantries together in an imaging configuration. The at least three mounting points (10) include at least one hinge (14) which permits the swivel gantry to swivel about the fixed gantry into a service configuration.

19 Claims, 6 Drawing Sheets

(51) Int. Cl.
   *A61B 6/03* (2006.01)
   *A61B 8/00* (2006.01)
   *A61B 5/055* (2006.01)
   *A61B 8/14* (2006.01)

(52) U.S. Cl.
   CPC .............. *A61B 8/14* (2013.01); *A61B 8/4416* (2013.01); *A61B 6/4411* (2013.01)

(56) References Cited

U.S. PATENT DOCUMENTS

| | | |
|---|---|---|
| 6,831,961 B1 | 12/2004 | Tybinkowski et al. |
| 7,603,165 B2 | 10/2009 | Townsend et al. |
| 7,941,203 B2 | 5/2011 | Zheng et al. |
| 8,139,713 B2 | 3/2012 | Janbakhsh |
| 9,313,867 B2 | 4/2016 | Sharpless |
| 2006/0202650 A1* | 9/2006 | Hausner ................ A61B 6/035 318/268 |
| 2010/0034350 A1 | 2/2010 | Vaisburd et al. |
| 2010/0290584 A1* | 11/2010 | Vesel .................... A61B 6/032 378/9 |
| 2013/0204113 A1 | 8/2013 | Carmi |

* cited by examiner

SWIVEL GANTRY FOR MULTI-MODAL IMAGING SYSTEMS

CROSS REFERENCE TO RELATED APPLICATIONS

This application is a national filing of PCT application Serial No. PCT/IB2013/055386, filed Jul. 1, 2013, published as WO 2014/013367 A2 on Jan. 23, 2014, which claims the benefit of U.S. provisional application Ser. No. 61/672,809 filed Jul. 18, 2012, which is incorporated herein by reference.

The following relates generally to medical imaging. It finds particular application in conjunction with multi-modal systems which include x-ray computed tomography (CT), positron emission tomography (PET), single photon emission computed tomography (SPECT), magnetic resonance (MR), and ultrasound (US), and the gantries which support those systems, and will be described with particular reference thereto. However, it will be understood that it also finds application in other usage scenarios and is not necessarily limited to the aforementioned application.

Each imaging modality such as CT, PET, SPECT, MR, and US has benefits and drawbacks. For example, CT provides anatomical detail, but is limited in providing metabolic or functional information. PET provides metabolic or functional information, but is limited in providing spatial anatomical detail. Increasingly, imaging modalities are combined to provide the benefits of both imaging modalities. Multi-modal systems which combine two or more imaging modalities typically utilize a separate gantry to implement each imaging modality. Each gantry contains the detectors and/or electronics for a modality. The gantries are typically separable to provide ease of maintenance, but may be contiguous to each other to facilitate image registration and patient movement through the imaging region of both modalities.

For example, in a CT/PET system, a bed or couch supports a patient as the bed moves through first a CT gantry, and then through a PET gantry. The CT gantry includes X-ray cameras or detectors. The PET gantry includes detectors which detect gamma photon emissions. The different modalities use different detector types. However, the isocenters of the gantries are aligned along a central axis to facilitate registration of images generated from each modality or in combination from both. Another example includes MR/PET. The gantry for the MR system includes the various coils such as the main magnet, the gradient coils, and the RF coils. The MR system also includes a cooling mechanism such as tubing which circulates a cryogen refrigerant which cools the coils to superconducting temperatures.

In order to facilitate maintenance, the gantries are typically separable. For example, in some CT/PET systems the heavier CT gantry is fixed, and the lighter PET gantry is placed on a set of precision rails which slide the PET gantry away from the CT gantry for servicing. The precision rails are designed to provide accuracy, repeatability, and ease of use. However, the distance between the two gantries in the open position is limited by the length of the rails. The length of the rails is limited by the size of the room, and cost. The rails also preclude other use of the space when not being serviced. Often, the distance allotted between the gantries in the open position makes servicing awkward. Equipment used to service the equipment must be lifted over the rails, and the personnel must work and move within the space between the gantries.

Furthermore, when there is a large height difference between the rails or sliding mechanism located on the floor use of rails complicates the alignment of isocenters which are at the relative height of the patient bed or couch. The difference is exasperated by dynamic loading on a cantilevered patient support as well as thermal changes.

The following discloses a new and improved swivel gantry for multi-modal imaging systems which addresses the above referenced issues, and others.

In accordance with one aspect, a multi-modal imaging system includes a fixed gantry, and a swivel gantry. The fixed gantry supports a first imaging modality. The swivel gantry connects to the fixed gantry by at least three mounting points and supports a second imaging modality. Selectively the swivel gantry includes a swivel frame and at least three mounting points for mounting the fixed and swivel gantries together in an imaging configuration. The at least three mounting points include at least one hinge which permits the swivel gantry to swivel about the fixed gantry into a service configuration.

In accordance with another aspect, a PET/CT imaging system includes a fixed gantry and a swivel gantry. The fixed gantry includes a plurality of detectors which detect x-rays and electronic circuitry which converts the detected x-rays into images. The swivel gantry connects to the fixed gantry by at least three mounting points. The swivel gantry includes a swivel frame, a plurality of detectors mounted to the swivel frame which detect emitted gamma photons, electronic circuitry which converts the detected emitted gamma photons into images, and at least three mounting points. The at least three mounting points include a hinge.

In accordance with another aspect, a PET/CT imaging system includes a CT gantry, a PET gantry, and a hinge assembly. The CT gantry defines an axial CT bore which has an isocenter. The PET gantry includes an annular PET detector array which defines an axial bore which has an isocenter. The hinge assembly (14) pivotally supports the PET gantry on the CT gantry to swivel between (a) an operating position in which the annular PET detector array is disposed in the axial CT bore with the PET and CT isocenters generally aligned and (b) a service position in which the PET gantry is swiveled about the hinge assembly away from the CT gantry to facilitate access to the CT and PET gantries for servicing.

One advantage is improved serviceability of the gantries with more open space.

Another advantage resides in ease of access to each gantry.

Another advantage resides in the flexibility of access options.

Another advantage resides in ease of alignment of the isocenters.

Another advantage includes reduced floor space requirements.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
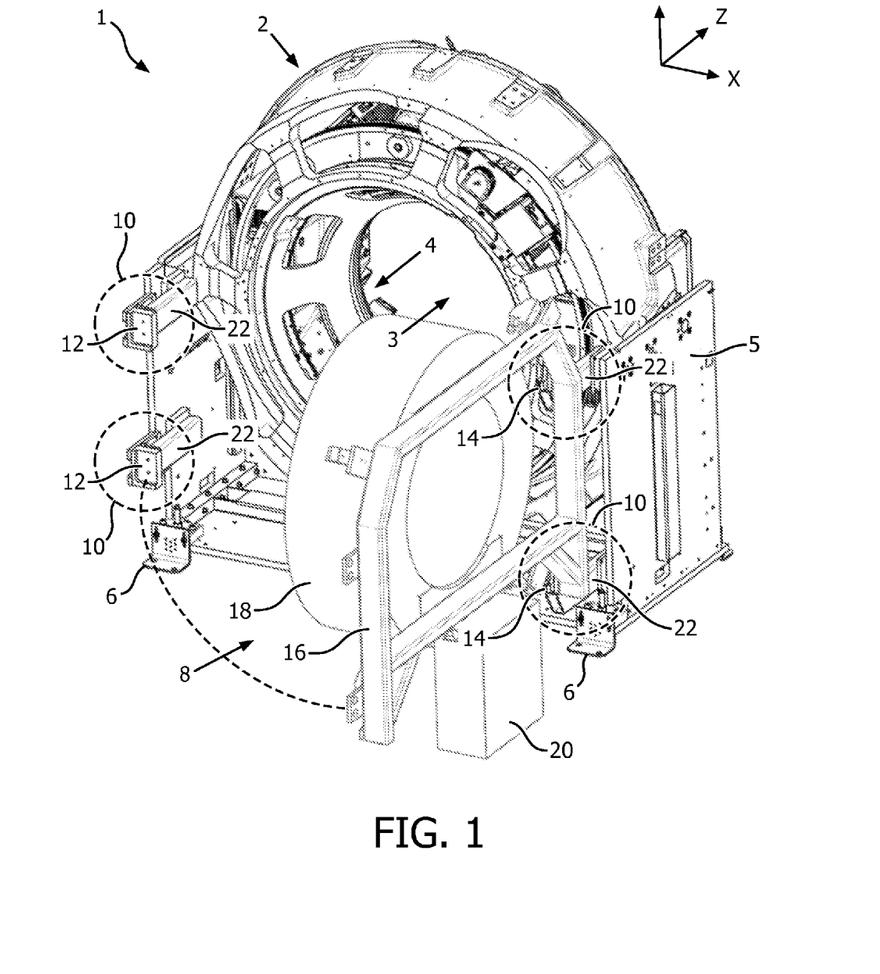
FIG. 1 schematically illustrates in perspective an embodiment of the multi-modal system with the swivel gantry in the open position with two hinges.

With reference to FIG. 1, an embodiment of the multi-modal system 1 with a swivel gantry in an open position is schematically illustrated. The multi-modal system 1 includes a gantry for each modality. The modalities include CT, MR, PET, SPECT, US and the like. The system includes a fixed gantry 2 which is shown without a cover. The fixed gantry is fixed in a stationary position and includes a bore opening 3 in the axial center of the gantry where an isocenter is located. A subject is moved into the bore opening during imaging by a patient support, bed, or couch (not shown). The fixed gantry includes detectors 4 attached to a fixed frame 5. The stationary position of the fixed gantry 2 can be maintained with floor mountings 6. The fixed gantry implements modalities such as CT, MR, PET, and the like. The selection of the modality for the fixed gantry involves considerations of weight, size, and other components. For example, in an MR gantry, the weight of the coils and coil cooling mechanisms favor a stationary or fixed gantry. The gantry for CT includes cameras or detectors which detect x-rays, an x-ray tube and oil based cooling system, a rotating gantry, and motors for rotating the gantry at high speeds, which also have considerable weight. A PET gantry includes a plurality of detectors circumferentially around an isocenter or bore. The weight and nature of the PET detectors allow either a fixed gantry or a swivel gantry. The amount, size, location, and nature of the circuitry mounted on the fixed and swivel gantries depend upon the implemented modality.

The system includes a swivel gantry 8 attached to the fixed gantry by at least three mounting points 10 to set its location and orientation relative to 3 orthogonal axes. In the embodiment shown, four mounting points are shown. Two mounting points include fixed mounting points 12 and two include hinges 14. The swivel gantry 8 swivels along an axis on one side of the gantry. The hinge or hinge assembly, hinges or hinge assemblies can be mounted on either side. The swivel gantry includes a frame 16 which is rigid in construction. Detectors 18 for the implemented modality of the swivel gantry such as a plurality of PET detectors or an annular PET detector array are attached to the frame 16. The swivel gantry detectors define a patient receiving bore with a swivel gantry isocenter. The subject is moved into the bore by a patient support (not shown) during imaging. Circuitry 20 to implement the second modality is attached to the frame. The amount, size, and nature of the circuitry 20 is specific to the modality implemented on the swivel gantry. In the embodiment shown, the swivel gantry opens approximately 90° or more for ease of access to both gantries. Other size degree openings are contemplated, but the floor space limitations may limit the arc of the swivel gantry. In addition, no hardware remains on the floor such as rails. The swivel gantry in the open or service position also provides ready access to the swivel and fixed gantries. There are no rails or other components to step over or lift equipment over. The axis of rotation for the swivel gantry can be to either side as may be more appropriate for the layout of the imaging room.

The mounting points 10 include brackets 22 which are adjustable. During initial set-up and calibration, the brackets are adjusted to align the isocenters of the fixed gantry 2 and the swivel gantry 8 when the swivel gantry is in the closed position. The adjustment mechanism, such as machine screws provides precise adjustment. For example, in a CT/PET system, the CT detectors are located on the fixed gantry and the PET detectors are located on the swivel gantry. The brackets are used to align the isocenter of the PET detectors with the isocenter of the CT detectors. The hinge assembly pivotally supports the PET gantry on the CT gantry to swivel between an operating position in which the PET detectors are disposed in the axial CT bore with the isocenters generally aligned and a service position in which the PET gantry is swiveled about the hinge assembly away from the CT gantry to facilitate access to the gantries for servicing.

Figure 2:
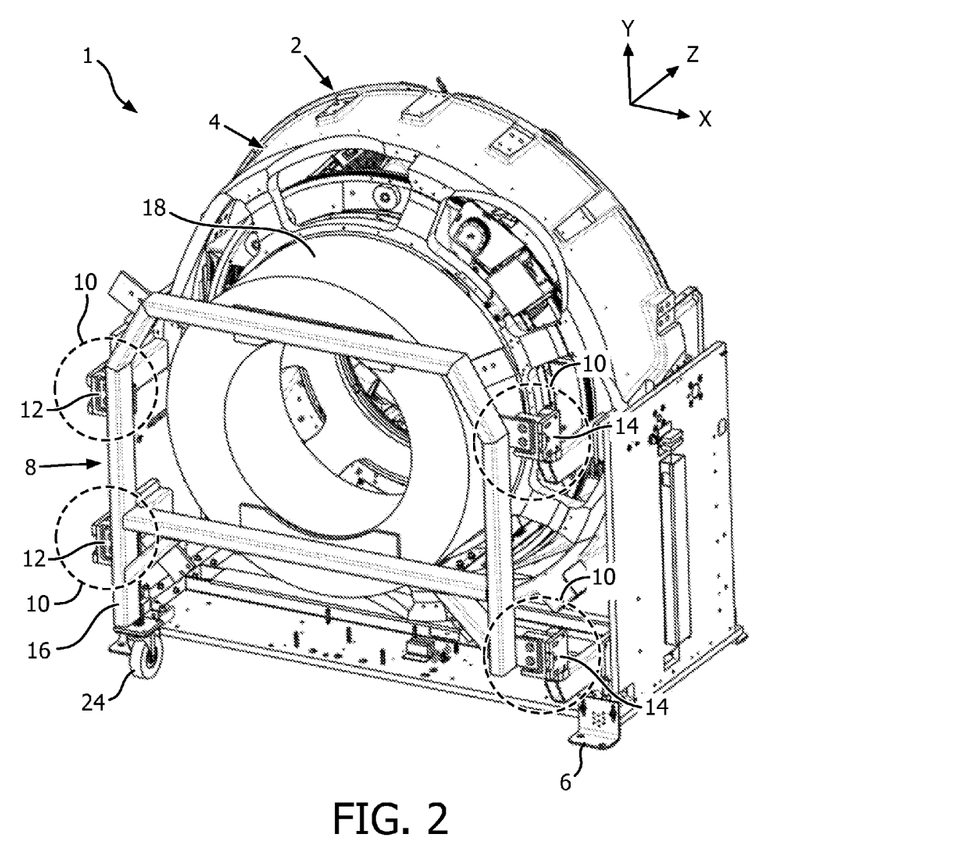
FIG. 2 schematically illustrates in perspective one embodiment of the multi-modal system with the swivel gantry and a supporting wheel assembly.

FIG. 2 schematically illustrates in perspective one embodiment of the multi-modal system 1 and the swivel gantry 8 with a supporting wheel assembly 24 and the circuitry not shown for simplicity of illustration. The swivel gantry can include one or more supporting wheel assemblies. The supporting wheel assembly 24 is connected to the swivel frame 16 and, in order to minimize the load applied onto the fixed gantry frame 5, provides support when the swivel gantry is attached to the fixed gantry, as well as when it is released from the mounting points on the side, particularly in the opening and open positions. The wheel assembly provides a nearly constant force even if the wheel assembly moves over irregularities in the floor.

Figure 3:
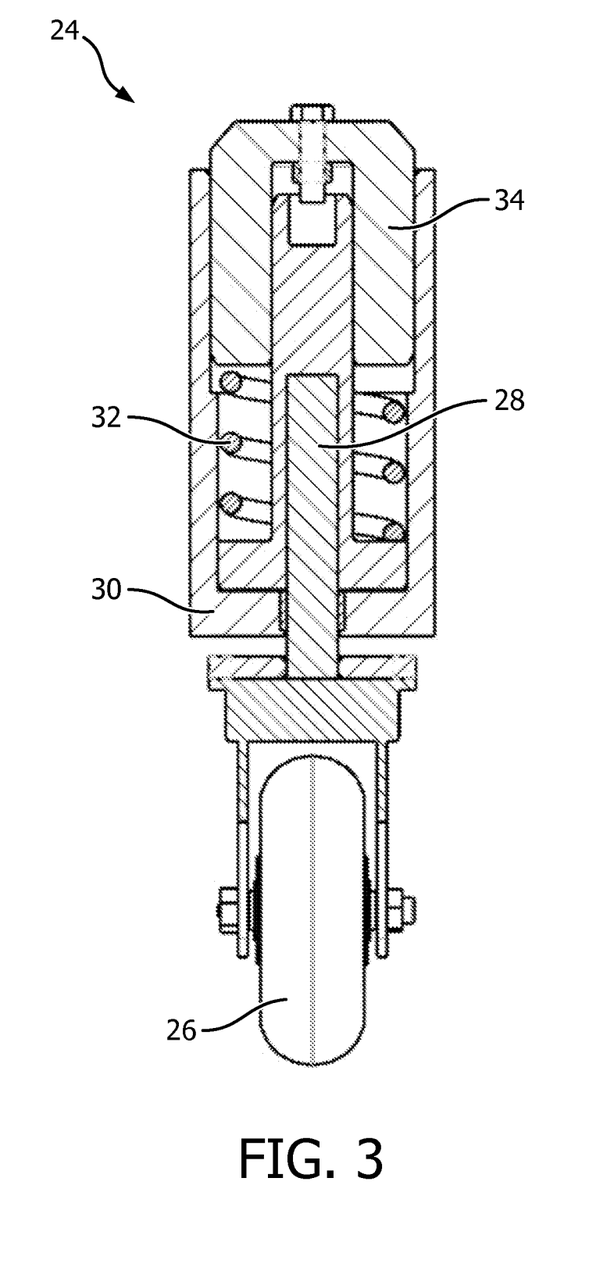
FIG. 3 schematically illustrates in a cross section one embodiment of the supporting wheel assembly.

FIG. 3 schematically illustrates in a cross section one embodiment of the supporting wheel assembly. The wheel assembly 24 includes a support wheel 26 connected by a moveable pin 28 which enables the wheel to rotate about a vertical axis. Though a swivel support wheel 26 is illustrated here, it is certainly possible to use non-swivel support wheels. The wheel assembly includes a fixed block 30 which is attached to the frame 16. The wheel assembly includes a spring 32 which is adjusted through an adjustment cap 34 to provide the nearly constant force. Threads between the cap and the block enable the compression of the spring to be adjusted. Other wheel assemblies are contemplated such as air suspension assemblies and the like. The supporting wheel assemblies are designed to apply minimal load to the fixed gantry 2 and ensure a supporting force close to the nominal value even through the floor is uneven along the trajectory of the wheel movement as the swivel gantry is opened. The contraction and expansion of the spring absorbs forces that could otherwise be transmitted to the hinge potentially adversely affect the calibration and alignment of the isocenters.

Figure 4:
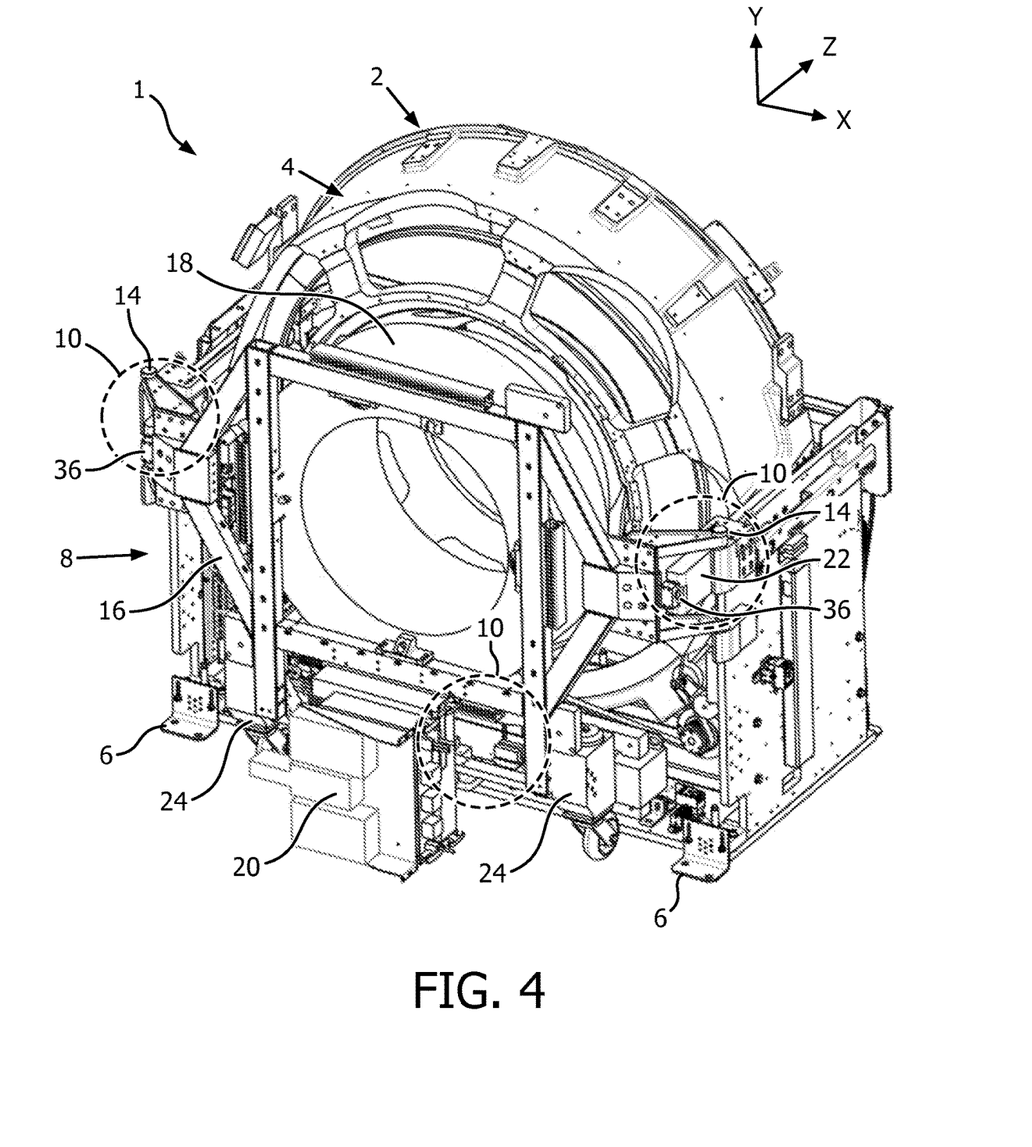
FIG. 4 schematically illustrates in perspective one embodiment of the multi-modal swivel gantry system with a single loose hinge, optionally two loose hinges at both sides, and at least three mounting points.

FIG. 4 schematically illustrates in perspective one embodiment of the multi-modal swivel gantry system with loose hinges. The system includes three mounting points 10. The mounting points are located at approximately the 3, 6, and 9 o'clock positions of the swivel gantry. The mounting point at the 6 o'clock position is a fixed mounting point. The mounting points at 3 o'clock and 9 o'clock positions each include a fixed mounting point and a hinge mechanism. The fixed mounting point operates only when the swivel gantry is in the closed position. In the embodiment, the electronic circuitry 20 are located in front of the 9 o'clock fixed mounting point. The amount, size, location, and nature of the electronic circuitry 20 depend upon the implemented modality. In this embodiment, the outer diameter of the hinge pin is slightly smaller than the inner diameter of the bearing hole. At the operating position, the swivel gantry 8 is attached to the fixed gantry 2 by the three fixed mounting points and by design there is still clearance between the hinge pin and the hinge bearing. After the swivel gantry 8 is separated from the fixed gantry 2 by disengaging the three fixed mounting points, the hinge will engage to facilitate the swivel. The hinge only support and restrain the swivel gantry 8 at opening and open positions. The fixed mounting points latch the swivel gantry to the fixed gantry at closed, i.e. operating, position. The swivel gantry can swivel open along one side axis or the other and open either direction such as left to right or right to left by removing the hinge shaft pin from one side. Only one direction is operable in the open position. In alternative embodiments, the hinge 14 is installed on one side or the other side either at the factory or customer site to open only on the selected single side. The mounting points operate in the closed position to align the isocenter of the swivel gantry 8 with the isocenter of the fixed gantry 2. Multiple supporting wheel assemblies 24 are shown connected to the frame 16.

Figure 5:
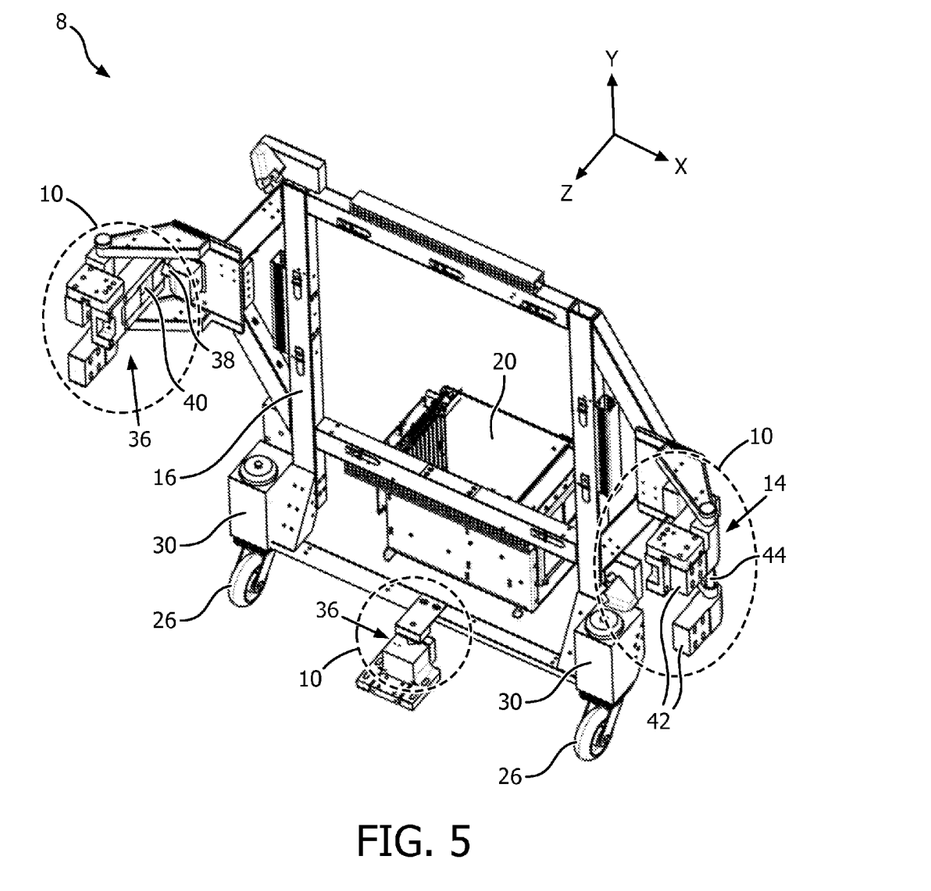
FIG. 5 schematically illustrates in different perspective the embodiment of the swivel gantry shown in FIG. 4 with detectors removed for simplicity of illustration.

FIG. 5 schematically illustrates in different perspective the embodiment of the swivel gantry 8 shown in FIG. 4 with the detectors not shown for simplicity of illustration. The fixed mounting point at 6 o'clock is shown with a latching mechanism 36. The fixed mounting point attaches the frame 16 of the swivel gantry 8 to the frame 5 of the fixed gantry 2. The at least three mounting points 10 include the hinge 14 at the 3 o'clock position, optionally another hinge 14 at the 9 o'clock position, and three latches 36 at the 9:00, 6:00 and 3:00 fixed mounting points. The mounting points are constructed to provide flexibility of movement in one direction in the coordinate axis and restraint in the other two directions. For example, the 9:00 latch 36 provides flexibility in the X direction and restrains movement in the Y and Z direction. The 6:00 latch provides flexibility in the Y direction and limits translation in the X and Z directions. The latch uses a mechanism such as a pin 38 and a leaf spring 40 to provide the flexibility in a direction orthogonal to a plane of the leaf spring and restrain movement in the other two directions.

The hinge 14 includes bearings 42 rotatably mounted a pin 44. In one embodiment the fit between the pin and the bearings is a tight sliding fit, such as the hinges of the embodiments shown in FIGS. 1 and 2. In another embodiment, the internal diameter of the bearings is slightly larger than the outer diameter of the mating pin such that the pin can move slightly inside the bearing, such as the hinges of the embodiments shown in FIGS. 4 and 5. The loose fit hinges are engaged to restrain the swivel when the swivel gantry 8 is in the opening and open positions, where the at least three fixed mounting points are disengaged. At operating position, the swivel gantry 8 is attached to the fixed gantry 2 by at least three fixed mounting points 10, where there is still clearance between the hinge bearing and the hinge shaft pin.

Figure 6A:
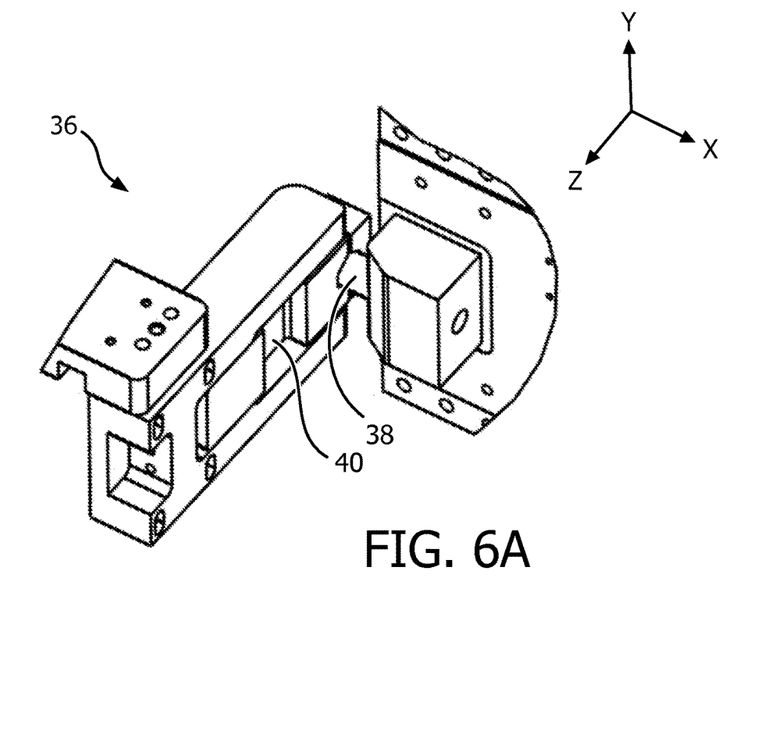
FIG. 6A schematically illustrates a perspective view and FIG. 6B a cross section view of one embodiment of the latching mechanism.
Figure 6B:
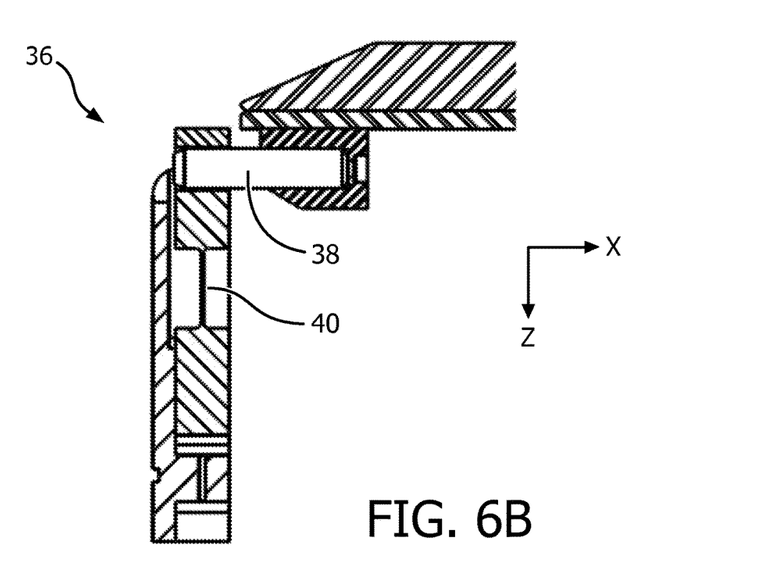

FIG. 6A schematically illustrates in perspective and FIG. 6B in a cross section one embodiment of the latching mechanism. The latch 36 includes a cylindrical pin 38 and a leaf spring 40. The pin 38 is mounted in a fixed position. In one embodiment, the pin includes an adjustment mechanism such as machine screws (not shown). In a closed position the swivel gantry moves the pin 38 into a receiving aperture in the leaf spring. The leaf spring provides flexibility in one direction shown as the X direction, but restrains movement in the Y and Z directions. The pin is clamped in the aperture to hold the swivel gantry in the closed position.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A multi-modal imaging system, comprising:
a fixed gantry which supports a first imaging modality;
a swivel gantry connected to the fixed gantry by at least three mounting points and supports a second imaging modality, the swivel gantry including:
a swivel frame;
at least three mounting points for mounting the fixed and swivel gantries together in an imaging configuration;
wherein the at least three mounting points include at least one hinge, the swivel gantry being configured to swivel about an axis of the hinge into an open configuration,
wherein in the imaging configuration, the second modality is disposed such that the first and second imaging modalities share a common imaging region and in the open configuration, the second imaging modality is displaced from the common imaging region.

2. The system according to claim 1, wherein the at least three mounting points include adjustable mounting brackets.

3. The system according to claim 2, wherein adjustable mounting brackets include an alignment mechanism.

4. The system according to claim 1, wherein the hinge is located with an axis of rotation on a side of the swivel gantry, the hinge and swivel gantry being configured such that at least a portion of the second imaging modality is disposed in a bore of the fixed gantry in the imaging configuration and out of the bore in the open configuration.

5. The system according to claim 1, wherein the at least three mounting points includes two hinges.

6. The system according to claim 1, wherein the at least three mounting points includes two hinges each hinge mounted on an opposite side of the swivel gantry each hinge associated with a selectively releasable pin which swivels the swivel gantry on either hinge by releasing pin of the other hinge.

7. The system according to claim 1, wherein the swivel gantry further includes:
one or more wheel assemblies attached to the swivel frame and the one or more wheel assemblies provide a supporting force.

8. The system according to claim 1, wherein the first modality includes one of:
computed x-ray tomography (CT);
magnetic resonance (MR) imaging.

9. The system according to claim 1, wherein the second modality includes one of:
positron emission tomography (PET):
single photon emission computed tomography (SPECT); and
ultrasound (US).

10. The system according to claim 1, wherein the fit between a hinge bearing and a hinge pin is a tight sliding fit.

11. The system according to claim 1, wherein each mounting point is adjustable along two directions of a coordinate axis.

12. The system according to claim 1, wherein at least one mounting point of the at least three mounting points is flexible along one coordinate axis direction and restrained in the remaining two directions.

13. The system according to claim 1, wherein each mounting point restrains translational movement relative to two axes of a coordinate system and provides adjustability relative to one axes of the coordinate system.

14. The system according to claim 1, wherein the at least one of mounting points include a latching mechanism limiting the translational movement of the swivel frame in two directions and providing flexibility in a third direction.

15. The system according to claim 14, wherein the latching mechanism includes a leaf spring.

16. A PET/CT imaging system, comprising:
a fixed gantry which defines a bore configured to receive a subject for imaging and includes:
an x-ray source mounted in the fixed gantry and configured to emit x-rays into the bore; and
an x-ray detector configured to detect x-rays from the x-ray source that have traversed the bore, the detector being mounted in the fixed gantry adjacent the bore;
a swivel gantry connected to the fixed gantry by at least three mounting points the swivel gantry includes:
a ring of PET detectors configured to detect gamma photons emitted by a radiopharmaceutical in the subject;
and
at least three mounting points including a hinge, the swivel gantry being configured to swivel at the hinge between a first position in the bore for PET or combined PET/CT imaging and a second position outside of the bore.

17. The PET/CT imaging system according to claim 16, wherein the at least three mounting points include adjustable brackets which align an isocenter of the plurality of the fixed gantry detectors with an isocenter of the plurality of the swivel gantry detectors.

18. The PET/CT imaging system according to claim 16, further including: at least one support wheel assembly attached to the swivel frame and the at least one support wheel assembly provides a supporting force.

19. A method of servicing a hybrid imaging system which includes a stationary gantry of a first modality scanner and a movable gantry of a second modality scanner that is connected to the stationary gantry by a hinge, the method comprising:
swiveling the movable gantry about the hinge to an open position for servicing;
after servicing, swiveling the movable gantry about the hinge to position a detector ring of the second modality scanner in a bore of the first modality scanner such that respective isocenters of the first and second modality scanners align in a common imaging region;
securing the movable gantry to the stationary gantry in at least three mounting points to fix a location and orientation of the detector ring in the bore of the first modality scanner.

* * * * *